United States Patent [19]

Genese

[11] 4,219,022
[45] Aug. 26, 1980

[54] EQUIPMENT SETS FOR THE SEQUENTIAL ADMINISTRATION OF MEDICAL LIQUIDS AT DUAL FLOW RATES HAVING PARALLEL SECONDARY LIQUID FLOWPATHS WHEREIN ONE SAID PATH IS CONTROLLED BY A LIQUID SEQUENCING VALVE

[75] Inventor: Joseph N. Genese, Waukegan, Ill.

[73] Assignee: Abbott Laboratories, North Chicago, Ill.

[21] Appl. No.: 16,232

[22] Filed: Feb. 28, 1979

[51] Int. Cl.² ............................................ A61M 5/14
[52] U.S. Cl. .............................. 128/214 G; 128/227; 137/113; 222/129.2; 222/145
[58] Field of Search ........... 128/214 R, 214 C, 214 G, 128/227, 214.2, 274; 222/129.2, 145; 137/112–114

[56] References Cited

U.S. PATENT DOCUMENTS

| | | | |
|---|---|---|---|
| 3,886,937 | 6/1975 | Bobo et al. | 128/214 G |
| 4,005,710 | 2/1977 | Zeddies et al. | 128/214 G |
| 4,105,029 | 8/1978 | Virag | 128/214 G |
| 4,116,646 | 9/1978 | Edwards | 55/159 |

*Primary Examiner*—Dalton L. Truluck
*Attorney, Agent, or Firm*—Robert L. Niblack; Aaron L. Hardt

[57] ABSTRACT

Equipment sets for the sequential administration of medical liquids wherein a primary liquid can be administered at a flow rate independent of the flow rate of a secondary liquid and prevent the inadvertent administration of air when the secondary liquid is depleted. The sets of this invention employ parallel flowpaths for the secondary liquid and a single liquid sequencing valve to control the flow of the primary liquid and the secondary liquid in one of the parallel flowpaths.

15 Claims, 9 Drawing Figures

EQUIPMENT SETS FOR THE SEQUENTIAL ADMINISTRATION OF MEDICAL LIQUIDS AT DUAL FLOW RATES HAVING PARALLEL SECONDARY LIQUID FLOWPATHS WHEREIN ONE SAID PATH IS CONTROLLED BY A LIQUID SEQUENCING VALVE

BACKGROUND OF THE INVENTION

The present invention relates to systems and equipment sets for the administration of medical liquids to a patient, and more particularly, to systems and equipment sets for the sequential administration of a plurality of medical liquids having parallel secondary liquid flowpaths, one of which is controlled by a liquid sequencing valve for the primary and secondary liquids.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250–2,000 ml. of the liquid. Such prolonged infusions commonly are administered at a flow rate of 10–150 ml./hr.

Frequently, the patient must receive an additive or secondary liquid while the prolonged infusion is being administered. Preferably, this secondary liquid should be administered through the same hypodermic needle to avoid unnecessary pain and trauma to the patient of additional vanipunctures. To avoid dilution and incompatability problems, it is also preferable that the flow of the primary liquid employed in the prolonged infusion be temporarily interrupted, the secondary liquid administered and the flow of the primary liquid resumed. Generally, the secondary liquid will be administered at a flow rate of 50–250 ml./hr.

Abbott Laboratories, North Chicago, Ill. manufactures a y-type set for the sequential administration of primary and secondary liquids. These VENOSET piggyback sets allow the prolonged infusion of a primary liquid to be temporarily halted by means of a backcheck valve in the primary liquid flow path to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corp., and entitled "Medical Administration Set for Dispensing Plural Medical Liquids". Another similar system is disclosed in U.S. Pat. No. 4,105,029 granted Aug. 8, 1978 to R. Virag, assigned to Baxter Travenol and entitled "Intravenous Solution Set Having An Air Access Site and Constricted Inner Diameter Portion".

An inherent disadvantage of the above-mentioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary liquid flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and secondary liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that an efficacious equipment set for the sequential administration of medical liquids at dual flow rates would be advantageous to the medical profession.

SUMMARY OF THE INVENTION

The primary object of the present invention, therefore, is to provide equipment sets for the sequential administration of medical liquids at dual flow rates that will not draw air from the secondary container when the secondary liquid has been depleted.

In accordance with this and other objects, there is provided by the present invention equipment sets for the sequential administration of medical liquids to a patient including a liquid sequencing valve, a primary tube, first and second secondary tubes, and a common tube all connected in fluid communication to form a primary liquid flow path and a pair of parallel secondary liquid flow paths. The primary liquid flow path includes the liquid sequencing valve and the primary and common tube. The secondary liquid flow path includes a first flow path comprising the first secondary tube and common tube and a second flow path comprising the first secondary tube, the liquid sequencing valve, the second secondary tube and the common tube.

To establish the dual flow rates of the primary and secondary liquids, a first flow control means on the common tube for adjusting the flow rate of the primary and secondary liquid flowing therethrough and a second flow control means in the second flow path for adjusting the flow rate of the secondary liquid are provided.

The liquid sequencing valve has a housing that has a liquid receiving chamber therein. Three passageways open directly into the chamber. A liquid impermeable valve means is normally positioned to close a first passageway and prevent the flow of liquid therethrough. The valve is hydrostatically moveable to a second position to open the first passageway and close a second passageway to the flow of liquid therethrough, whenever the pressure of secondary liquid in the chamber exceeds the pressure of primary liquid in the chamber.

Thus, primary liquid is allowed to flow from the primary container whenever the height of primary liquid is greater than or equal to the height of secondary liquid in the system and prevented from flowing whenever the height of primary liquid is less than the height of the secondary liquid. When the valve means covers the first passageway, primary liquid flowing through the primary liquid flow path prevents the first or second secondary tube from completely emptying and insures that no air is drawn through the secondary flow path from the secondary container when the secondary liquid is depleted.

The third passageway is open to the flow of liquid therethrough regardless of the position of the valve means. The liquid sequencing valve can have an H or X-shaped housing including fourth and fifth passageways having an opening in fluid communication with the third passageway.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein.

Detailed Description of the Invention

Figure 1:
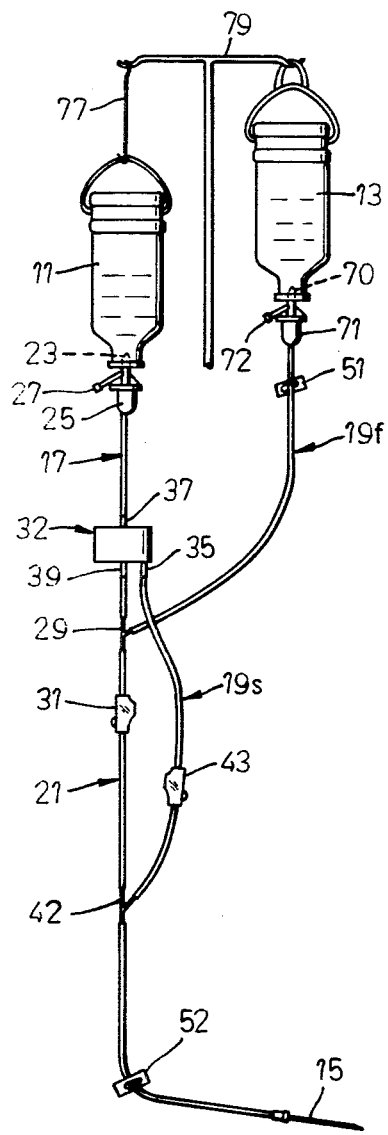
FIG. 1 is a front elevational view of an equipment set for the sequential administration of medical liquids at dual flow rates contemplated by this invention.

Referring to the drawing, there is shown in FIG. 1, the basic elements of the equipment sets for the sequential administration of medical liquids at dual flow rates contemplated by this invention. FIG. 1 depicts a primary liquid container 11 that contains a primary medical liquid to be administered to a patient for a prolonged period of time. FIG. 1 also depicts a secondary liquid container 13 that contains a secondary medical liquid to be administered to the patient for a relatively short period of time, during which time the administration of the primary liquid will be temporarily interrupted. Containers 11 and 13 can be glass bottles, plastic flexible bags, or any other suitable container.

The distal end of a primary tube 17 is in fluid communication with primary container 11, preferably by means of a piercing pin 23 inserted into a puncturable closure of container 11. Piercing pin 23 can have an integral drip chamber 25, and when container 11 is a glass bottle, as shown in the set of FIG. 1, an integral, filtered air vent 27. Such piercing pins, drip chambers and air vents are well known in the medical practice and need not be more fully explained here.

Figure 2:
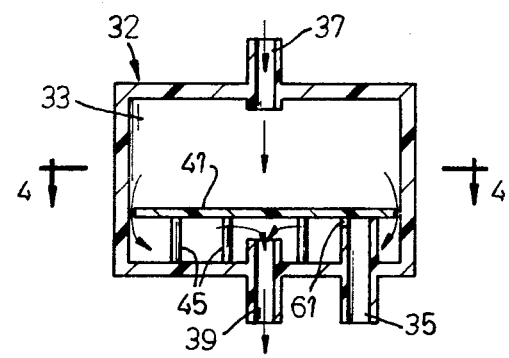
FIGS. 2-3 are front elevational views in cross-section illustrating the operation of one embodiment of the liquid sequencing valve.
Figure 3:
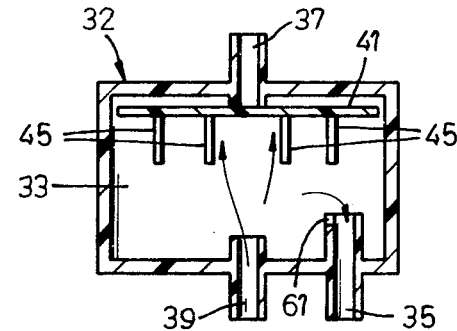
Figure 4:
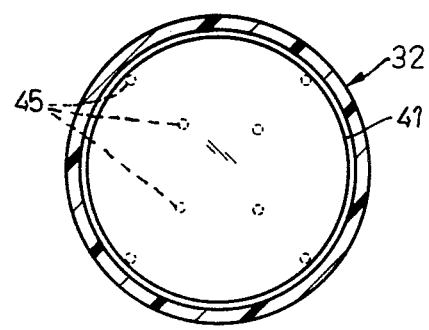
FIG. 4 is a cross-sectional view of the liquid sequencing valve of FIG. 2 along line 4—4 thereof.

A liquid sequencing valve having a housing 32 is shown in FIG. 1. Housing 32 has a liquid receiving chamber 33, as illustrated in FIG. 2. Chamber 33 has first, second, and third passageways 35, 37, 39 opening therein through housing 32. A liquid impermeable valve means 41 is positioned within chamber 33 so that it normally closes first passageway 35. Valve means 41 is hydrostatically moveable to a second position to open first passageway 35 and close second passageway 37 to the flow of liquid therethrough, as illustrated in FIG. 3. Third passageway 39 is open to the flow of liquid therethrough regardless of the position of valve means 41.

The proximal end of primary tube 17 is joined in fluid communication to the distal end of second passageway 37. The distal end of common tube 21 is joined in fluid communication to the proximal end of third passageway 39, preferably, by a y-tube 29.

The distal end of a first secondary tube 19f is in fluid communication with secondary container 13, preferably, by means of a piercing pin 70 inserted into a puncturable closure of container 13. Piercing pin 70 can have an integral drip chamber 71, and when container 13 is a glass bottle, as shown in FIG. 1, an integral, filtered air vent 72. The proximal end of first secondary tube 19f is joined in fluid communication to the distal end of common tube 21 and the proximal end of third passageway 39, preferably, by a y-tube 29.

A second secondary tube 19s has its distal end connected in fluid communication with the proximal end of first passageway 35 of housing 32. The proximal end of second secondary tube 19s is connected in fluid communication with common tube 21 at a site intermediate the ends thereof, preferably, by a y-tube 42.

Thus, a primary liquid flow path is formed between primary liquid container 11 and a conventional hypodermic needle 15 through primary tube 17, second passageway 37, chamber 33, third passageway 39 and common tube 21. Likewise, a secondary liquid flow path is formed between secondary liquid container 13 and needle 15 by parallel first and second flow paths. The first flow path comprises first secondary tube 19f and common tube 21. The second flow path comprises first secondary tube 19f, third passageway 39, chamber 33, first passageway 35, second secondary tube 19s and common tube 21.

A first flow control 31 is located on common tube 21 between y-tubes 29, 42. First flow control 31 can be adjusted to vary the flow rate of primary or secondary liquid flowing through the primary liquid flow path and the first secondary liquid flow path. A second flow control 43 is disposed at any convenient location in the second secondary liquid flow path for adjusting the rate of flow of secondary liquid therethrough. Preferably, as shown in FIG. 1, first and second flow controls 31, 43 can be roller clamps. However, they can be any other adjustable devices that can reliably maintain a desired secondary liquid flow rate.

Valve means 41 can be made of any liquid impermeable material, such as natural or silicone rubber, or thermoplastic materials such as polyethylene. Valve means 41 can be captured between joined halves of housing 32, or alternatively, valve means 41 can be insert molded inside an integral housing 32. Valve means 41, preferably, is a poppet valve which normally covers first passageway 35, as shown in FIG. 2 and can have a plurality of legs 45. However, whenever the pressure of secondary liquid on valve means 41 is greater than the pressure of primary liquid on valve means 41, it will float or hydrostatically move away from first passageway 35 and cover second passageway 37, as shown in FIG. 3.

Thus, valve means 41 allows primary liquid to flow from primary container 11 whenever the height of the primary liquid is greater than or equal to the height of the secondary liquid in the system of FIG. 1. Further, valve means 41 prevents the flow of primary liquid from primary container 11 whenever the height of the primary liquid is less than the height of the secondary liquid in the system. When valve means 41 covers first passageway 35, primary liquid flowing through the primary liquid flow path prevents the liquid in either first secondary tube 19f or second secondary tube 19s from completely emptying and thus, while the set is in use, prevents the flow of air through the secondary flow path whenever the secondary liquid in secondary container 13 is depleted.

Optionally, first passageway 35 can be provided one or more minute apertures 61 at its end in chamber 33. The aperture 61 will be open to the flow of liquid therethrough regardless of the position of valve means 41 and prevent valve means 41 from becoming locked onto first passageway 35 by the column of liquid standing in second secondary tube 19s while primary liquid is flowing through the primary liquid flow path.

Figure 5:
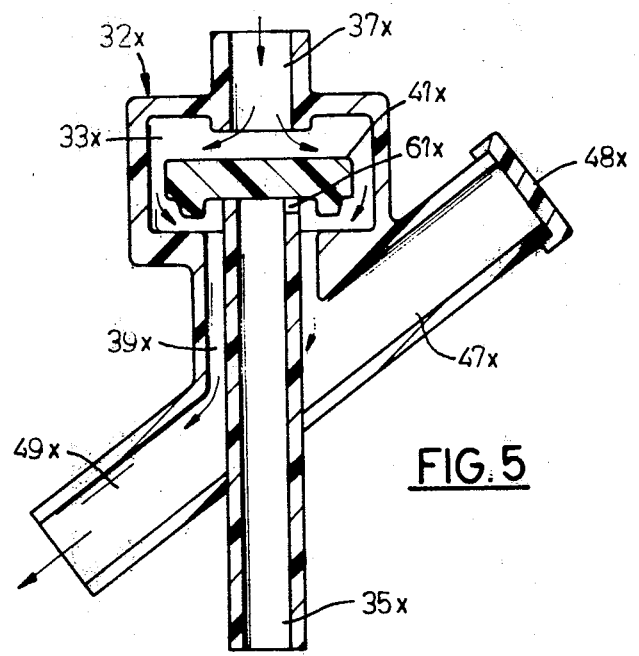
FIGS. 5-6 are front elevational views in cross-section illustrating the operation of another embodiment of the liquid sequencing valve.
Figure 6:
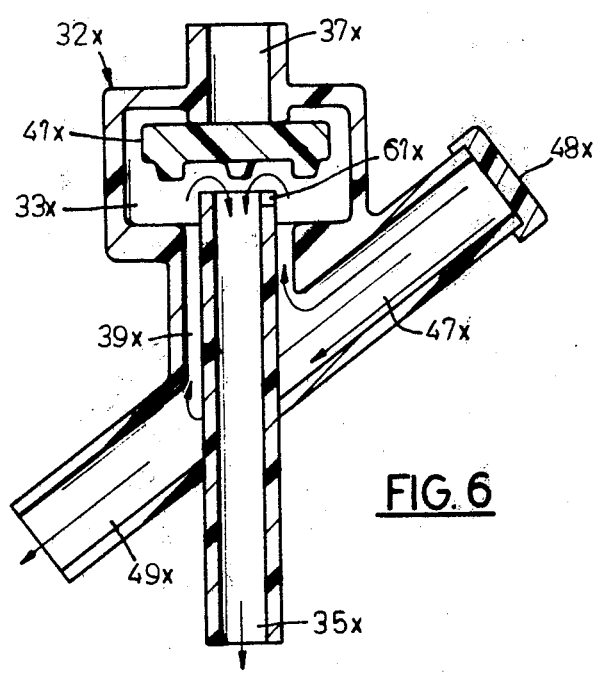

As shown in FIGS. 5 and 6, the liquid sequencing valve housing 32 can be incorporated into y-tube 29 to form a novel X-shaped liquid sequencing valve. X-shaped housing 32x has a liquid receiving chamber 33x which has three passageways 35x, 37x, 39x thereto.

A portion of first passageway 35x is concentric to and within third passageway 39x and, optionally, has an aperture 61x at its end in chamber 33x. A fourth passageway 47x closed at one end thereof by a resealable membrane 48x has its opposite end in fluid communication with the proximal end of third passageway 39x. A fifth passageway 49x is open at one end thereof and has its opposite end in fluid communication with the proximal end of third passageway 39x and the opposite end of passageway 47x.

A liquid impermeable valve means 41x is positioned within chamber 33x so that it normally closes first passageway 35x to the flow of liquid therethrough. Valve means 41x is hydrostatically moveable to a second position to open first passageway 35x and close second passageway 37x to the flow of liquid therethrough, as illustrated in FIG. 6. Third passageway 39x is open to the flow of liquid therethrough regardless of the position of valve means 41x.

Preferably, housing 32x is made of a plurality of plastics parts solvent sealed or welded together into an integral unit. Valve means 41x is, preferably, a poppet valve having legs 45x which orient it with regard to its normally closed position over first passageway 35x. U.S. Pat. No. 4,005,710 granted to A. Zeddies, et al. on Feb. 1, 1977 discloses a one-way valve useful with medical liquids and a description of its manufacture. The teachings of the Zeddies patent are incorporated herein by this reference thereto.

Figure 7:
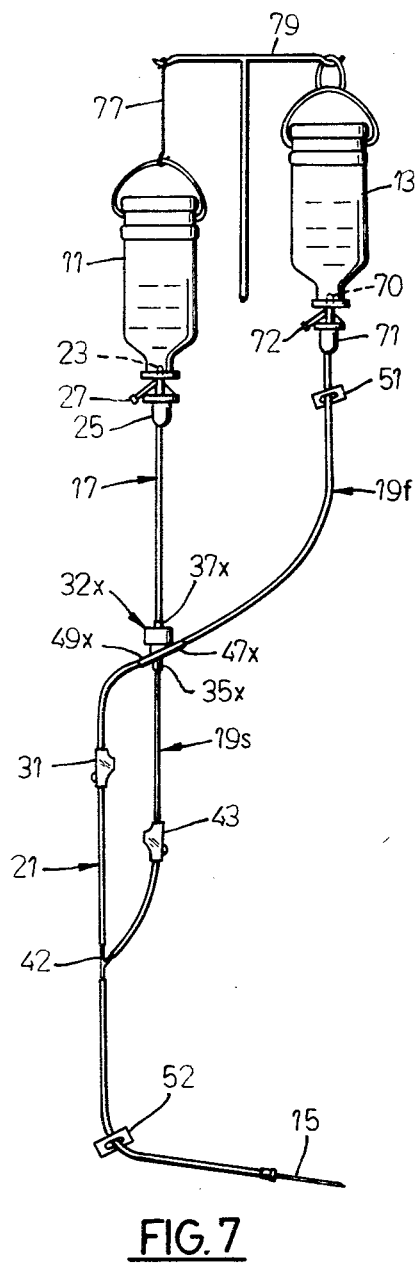
FIG. 7 is a front elevational view of an equipment set for the sequential administration of medical liquids at dual flow rates employing the liquid sequencing valve of FIGS. 5-6, and FIGS. 8-9 are front elevational views in cross-section illustrating the operation of another embodiment of the liquid sequencing valve.

When liquid sequencing valve housing 32x is incorporated into the set of FIG. 1, it will appear as shown in FIG. 7. Primary tube 17 is conected to second passageway 37x, first secondary tube 19f is connected to fourth passageway 47x through resealable membrane 48x, second secondary tube 19s is connected to first passageway 35x and common tube 21 is connected to fifth passageway 49x. It will be readily apparent that fourth passageway 47x and fifth passageway 49x have the same function respectively as the first secondary tube leg and common tube leg of ytube 29 do in the set of FIG. 1.

Figure 8:
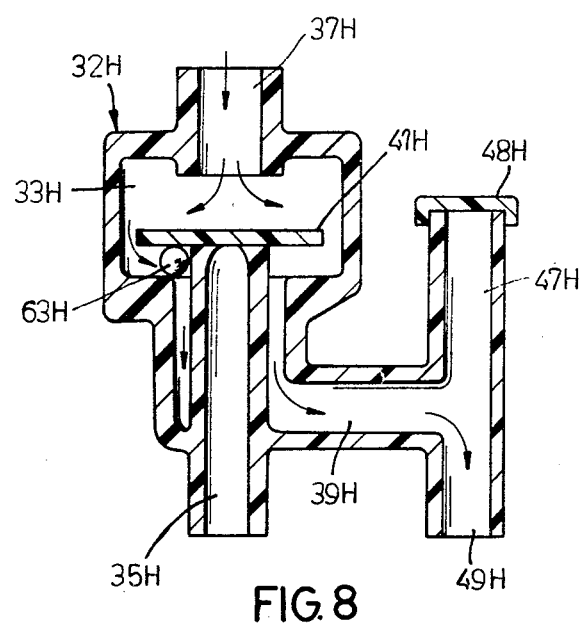
Figure 9:
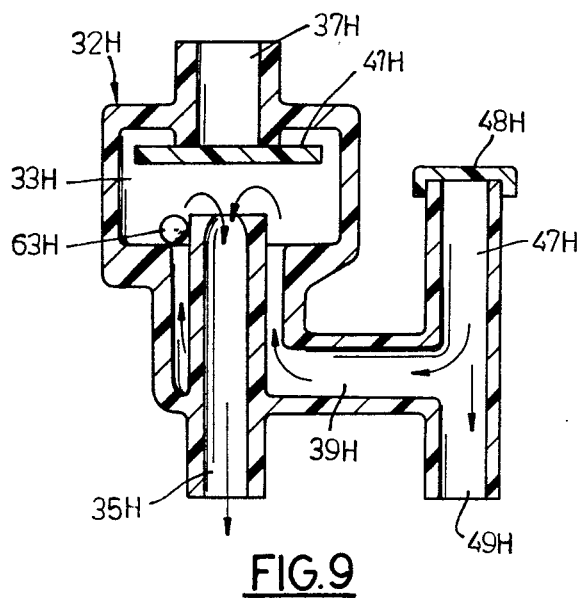

As shown in FIGS. 8 and 9, the liquid sequencing valve housing 32 can be incorporated into y-tube 29 to form a novel H-shaped liquid sequencing valve. H-shaped housing 32H has a liquid receiving chamber 33H which has three passageways 35H, 37H, 39H thereto.

A portion of first passageway 35H is concentric to and within third passageway 39H. A fourth passageway 47H closed at one end thereof by a resealable membrane 48H has its opposite end in fluid communication with the proximal end of third passageway 39H. A fifth passageway 49H is open at one end thereof and has its opposite end in fluid communication with the proximal end of third passageway 39H and the opposite end of passageway 47H.

A liquid impermeable valve means 41H is positioned within chamber 33H so that it normally closes first passageway 35H to the flow of liquid therethrough. Valve means 41H is hydrostatically movable to a second position to open first passageway 35H and close second passageway 37H to the flow of liquid therethrough, as illustrated in FIG. 9. Third passageway 39H is open to the flow of liquid therethrough regardless of the position of valve means 41H.

Preferably, housing 32H is made of a plurality of plastics parts solvent sealed or welded together into an integral unit. Valve means 41H is, preferably, a disc-shaped poppet valve. A, preferably, stainless steel ball 63H is provided in chamber 33H, below valve means 41H. Ball 63H will have sufficient density not to float and normally will be seated on the bottom of chamber 33H against first passageway 35H. During the priming of the set, housing 32H will be inverted and the weight of ball 63H will insure that valve means 41H does not seat over first passageway 35H until housing 32H is returned to its upright position. More than one such ball can be provided.

When liquid sequencing valve housing 32H is incorporated into the set of FIG. 1, primary tube 17 is connected to second passageway 37H, first secondary tube 19f is connected to fourth passageway 47H through resealable membrane 48H, second secondary tube 19s is connected to first passageway 35H and common tube 21 is connected to fifth passageway 49H.

It will be readily apparent that fourth passageway 47H and fifth passageway 49H have the same function respectively as the first secondary tube leg and common tube leg of y-tube 29 in the set of FIG. 1. Also, it will now be apparent to those skilled in the art that various configurations other than an H or X can be employed for the housing 32 of the liquid sequencing valve of this invention.

The sets of FIGS. 1 and 7 include a slide clamp 51 near the distal end of secondary tube 19f and a slide clamp 52 near the proximal end of common tube 21.

For simplicity, the equipment sets of this invention have been depicted and described as integral units. It is apparent, however, that the sets can be manufactured and assembled in subsets of the entire set and that each subset will accordingly be provided such resealable closures, piercing means, adapters, etc. as are necessary to permit their easy assemblage into the complete set at an appropriate time.

Operation of the System

As depicted in FIGS. 1 and 7, primary container 11 is suspended in space at a height above the patient by means of a hook 77 and stand 79. It will be apparent that other means for suspending the containers of this invention are well known.

To insure that all the air that might be forced into the patient has been removed from the sets, the sets are initially primed by first closing slide clamps 51 and 52. Piercing pin 23 is then inserted into the resealable closure of primary container 11. Slide clamp 52 and flow controls 31 and 43 are then opened and liquid sequencing valve housing 32 is held in an inverted position. Primary liquid will then flow through primary tube 17 into chamber 33 until it is full, then through third passageway 39 into common tube 21 and concomittantly through first passageway 35 into second secondary tube 19s, then into common tube 21. Slide clamp 52 is then closed and slide clamp 51 opened. Primary liquid will then flow into first secondary tube 19f and force all the air therefrom that might be forced into the patient. Slide clamp 51 is then closed, housing 32 returned to an upright position and first secondary tube 19f stored in a convenient location.

Common tube 21, which preferably has an adapter at its proximal end open to the flow of liquid therefrom, is next connected to needls 15, which will generally have been already inserted into a vein of the patient. Slide clamp 52 will then be opened to allow primary liquid to flow through the primary liquid flow path to the patient's vein. The weight of primary liquid flowing over valve means 41 will further bias valve means 41 against first passageway 35. First flow control 31 is then adjusted to a setting that will provide the desired flow rate for a prolonged infusion of primary liquid into the patient, generally 10-150 ml./hr. As is well known in the medical practice, that flow rate can be visually observed by viewing and counting drops passing through the primary drip chamber 25.

Subsequently, when it is desired to administer a secondary liquid to a patient, if first secondary tube 19f has not yet been attached, it is attached to either the appropriate leg of y-tube 29 or fourth passageway 47, slide clamp 51 opened and slide clamp 52 closed to allow primary liquid to flow into first secondary tube 19f and force all the air therefrom that might be forced into the patient. Slide clamp 51 is then closed and slide clamp 52 opened.

Then, piercing pin 70 at the distal end of secondary tube 19 will be inserted into the resealable closure of secondary container 13. Secondary container 13 is then suspended in space from stand 79 at a height substantially greater than the height of primary container 11 and slide clamp 51 is opened. Secondary liquid will then immediately begin to flow through the secondary liquid flow path. The pressure of secondary liquid on valve means 41 is greater than the pressure of the primary liquid and will force valve means 41 away from first passageway 35 against and over second passageway 37 to prevent the flow of primary liquid from primary container 11. Secondary flow control 43 is then adjusted to a desired flow rate, typically 50-250 ml./hr., for the secondary liquid, which will then flow until the liquid in secondary container 13 is depleted.

When the height of primary liquid in the sets of FIGS. 1 and 7 becomes greater than the height of the secondary liquid, valve means 41 will immediately move away from second passageway 37 and allow primary liquid to flow from primary container 11 at the flow rate to which first flow control 31 is adjusted. Valve means 41 will then return to its normally closed position covering first passageway 35 and providing a substantially impermeable barrier to liquid in the second liquid flow path.

When primary container 11 becomes depleted of primary liquid, the primary piercing pin 23 is merely removed therefrom and inserted into the resealable closure of a new primary container, which is then suspended in place of the previous container. If primary container 11 had completely emptied before it was replaced, it will be necessary to prime primary tube 17 in the manner by which it was initially primed.

When secondary container 13 becomes depleted of secondary liquid, it can be left empty until another secondary liquid is to be administered. When another secondary liquid is to be administered, the secondary piercing pin 70 is merely removed from secondary container 13 and inserted into a new secondary liquid container and the priming procedure used for initiating the flow of secondary liquid from the first secondary container repeated.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

I claim:

1. A set for the sequential administration of medical liquids to a patient, comprising:

a liquid sequencing valve defined by a housing having a chamber therein, first, second and third pasageways opening into said chamber, and a liquid impermeable valve means normally positioned to close said first passageway to the flow of liquid therethrough, said valve means hydrostatically moveable to a second position to open said first passageway and close said second passageway to the flow of liquid therethrough, and said third passageway open to the flow of liquid therethrough regardless of the position of said valve means, a primary tube for the flow of a primary medical liquid therethrough having the proximal end in fluid communication with said second passageway, a first secondary tube for the flow of a secondary medical liquid therethrough having its proximal end in fluid communication with said third passageway, a common tube having its distal end in fluid communication with the proximal end of said first secondary tube and said third passageway and its proximal end open for the flow of liquid therefrom, a second secondary tube for the flow of said secondary liquid therethrough having its distal end in fluid communication with said first passageway and its proximal end in fluid communication with said common tube at a site intermediate the ends thereof, whereby a primary liquid flow path is formed by said primary tube, said second passageway, said chamber, said third passageway and said common tube and a secondary liquid flow path is formed by a first flow path comprising said first secondary tube and said common tube and a second flow path comprising said first secondary tube, said third passageway, said chamber, said first passageway, said second secondary tube and said common tube, a first flow control means on said common tube distal to said site intermediate the ends thereof for adjusting the flow rate of primary and secondary liquid flowing therethrough, and a second flow control means in said second flow path for adjusting the flow rate of secondary liquid flowing therethrough, whereby said secondary liquid flows through said secondary liquid flow path at a rate controlled by said first and second flow control means and said primary liquid flow through said primary liquid flow path at a rate independent of the flow rate of said secondary liquid.

2. The set defined in claim 1, wherein said liquid sequencing valve has a substantially H or X-shaped housing, at least a portion of said first passageway is concentric to and within said third passageway, and said housing has fourth and fifth passageways therethrough each having an opening in fluid communication with said third passageway to said chamber, said proximal end of said first secondary tube being connected directly to said fourth passageway and said distal end of said common tube being connected directly to said fifth passageway.

3. The set defined in claim 2, wherein said fourth passageway is covered at one end thereof by a resealable membrane.

4. The set defined in claim 1, 2, or 3, wherein said first passageway has a minute aperture open to the flow of liquid therethrough regardless of the position of said valve means.

5. The set defined in claim 1, 2 or 3, wherein said valve means is a poppet valve.

6. The set defined in claim 1 or 2, wherein said primary tube has a piercing pin at its distal end.

7. The set defined in claim 6, wherein said secondary tube has a piercing pin at its distal end.

8. The set defined in claim 7, wherein said piercing pin of said primary and secondary tube have drip chambers integral therewith.

9. The set defined in claim 7, wherein said piercing pins of said primary and secondary tube have air vents integral therewith.

10. A set for the sequential administration of medical liquids to a patient, comprising:

a liquid sequencing valve defined by an H or X-shaped housing having a chamber therein, first, second and third passageways opening into said chamber, at least a portion of said first passageway concentric to and within said third passageway, a liquid impermeable poppet valve normally positioned to close said first passageway and prevent the flow of liquid therethrough, said poppet valve hydrostatically moveable to a second position to open said first passageway and close said second passageway to prevent the flow of liquid therethrough, said third passageway open to the flow of liquid therethrough regardless of the position of said poppet valve, and fourth and fifth passageways through said housing each having an opening in fluid communication with said third passageway to said chamber, a primary tube for the flow of a primary medical liquid therethrough having its proximal end in fluid communication with said second passageway, a common tube having its distal end in fluid communication with said fifth passageway and its proximal end open for the flow of liquid therefrom, a secondary tube for the flow of a secondary medical liquid therethrough having its distal end in fluid communication with said first passageway and its proximal end in fluid communication with said common tube at a site intermediate the ends thereof, and said fourth passageway covered at one end by a resealable membrane, whereby a primary liquid flow path is formed by said primary tube, said second passageway, said chamber, said third and fifth passageways and said common tube and a secondary liquid flow path is formed by a first flow path comprising said fourth and fifth passageways and said common tube and a second flow path comprising said fourth passageway, said third passageway, said chamber, said first passageway, said secondary tube and said common tube;

a first flow control means on said common tube distal to said site intermediate the ends thereof for adjusting the flow rate of primary and secondary liquid flowing therethrough, and a second flow control means on said secondary tube for adjusting the flow rate of secondary liquid flowing therethrough, whereby said secondary liquid flows through said secondary liquid flow path at a rate controlled by said first and second flow control means and said primary liquid flows through said primary liquid flow path at a rate independent of the flow rate of said secondary liquid.

11. The set defined in claim 10, wherein said first passageway has a minute aperture open to the flow of liquid therethrough regardless of the position of said valve means.

12. The set defined in claim 10 or 11, wherein said primary tube has a piercing pin at its distal end.

13. The set defined in claim 12, wherein said piercing pin has a drip chamber integral therewith.

14. The set defined in claim 12, wherein said piercing pin has an air vent integral therewith.

15. The set defined in claim 1 or 10 and further including a ball having a density greater than water normally disposed at the bottom of said chamber and below said valve means whenever said housing is in a upright position.

* * * * *